Jan. 31, 1950 E. B. LE GRICE Plant Pat. 917
ROSE PLANT
Filed Jan. 17, 1949
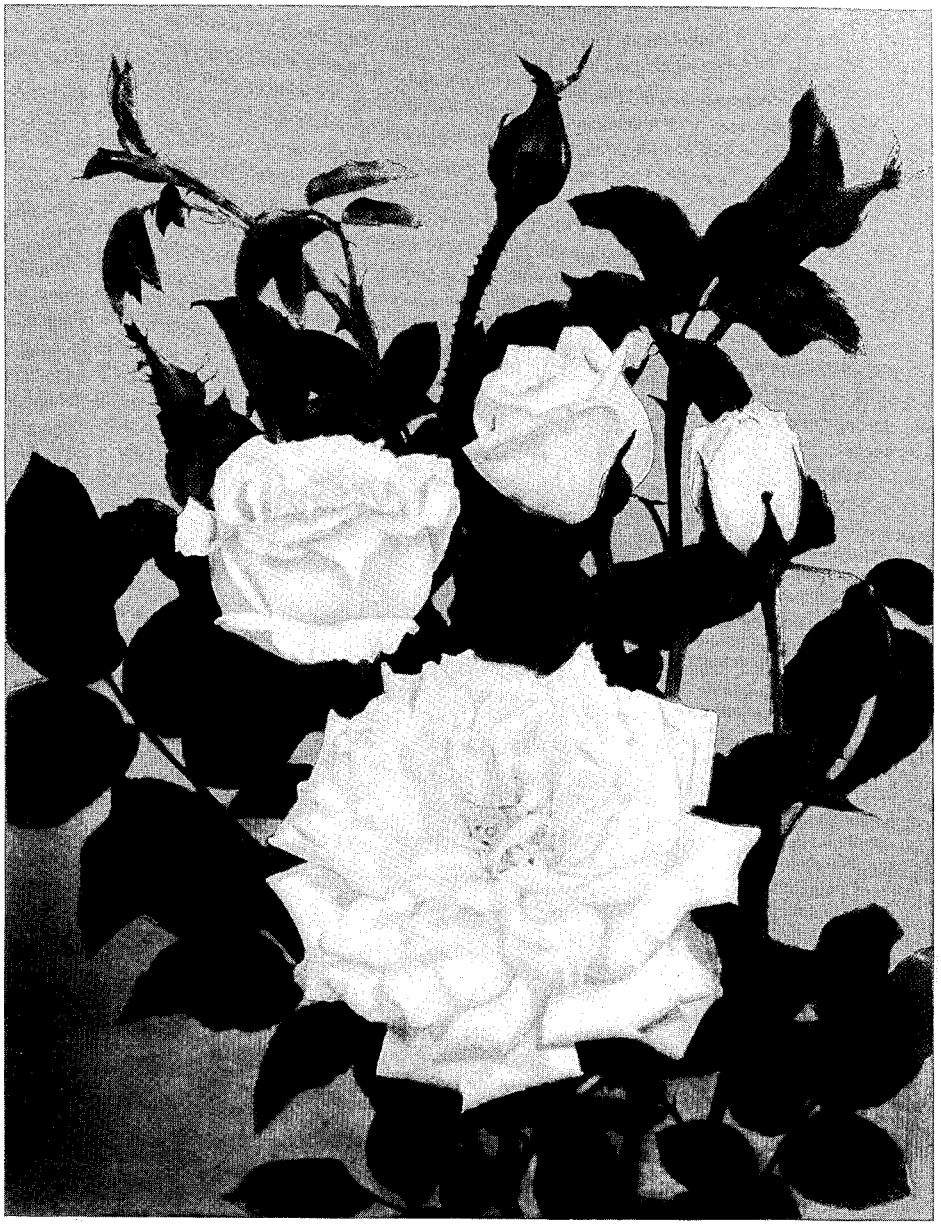
Inventor
E. B. LeGrice
By Robert Cobb
Attorneys Patented Jan. 31, 1950

UNITED STATES PATENT OFFICE

917

ROSE PLANT

Edward Burton Le Grice, North Walsham, England, assignor to Jackson & Perkins Company, Newark, N. Y., a corporation of New York Application January 17, 1949, Serial No. 71,378

1 Claim. (Cl. 47—61)

The present invention relates to a new and distinct variety of hybrid tea rose plant, resulting from a cross between the varieties "Lillian" and "Golden Dawn," and primarily noted for the clear, clean, yellow color of its blooms.

In addition to the above mentioned important feature, this new variety is characterized as to novelty by the following combination of characters: its unusually long peduncle well shown in the accompanying illustration; the peculiar coloring of the stamens, as hereinafter more specifically described; and the glossy and leathery foliage which sets off the yellow coloring of the bloom very strikingly.

Asexual reproduction of this new variety shows the foregoing characteristics come true to form and are established.

In the drawing is shown a group of specimens of the flowers and foliage at different stages of development from bud to full blown blooms.

The following is a detailed description of the new variety, color terminology being in accordance with Ridgway's Color Standards and Nomenclature:

Parentage: Seedling.

*Seed parent.*—"Lillian" (unpatented).

*Polen parent.* — "Golden Dawn" (unpatented).

Classification: Botanic and commercial—hybrid tea.

*Flower*

Observations made in greenhouse at Newark, New York, in the month of September in the afternoon.

Blooming habit: Recurrent—continuous.

Bud:

*Size.*—Large.

*Form.*—Oviod. Is not affected by wet or hot weather.

*Color.*—When sepals first divide—Oxblood Red, Plate 1. When petals begin to unfurl—Ochraceous Salmon, Plate 15. When half blown—Inside of petals: Light Orange Yellow, Plate 3; reverse of petals: Apricot Yellow, Plate 4.

*Sepals.* — Serrated, branched. Curl back when petals begin to unfurl. Color—inside: Pale Veronese Green, Plate 18; outside: Parrot Green, Plate 6.

*Calyx.*—Shape—pear. Size—small. Aspect smooth. Odor when rubbed — none. Color—Yellowish Oil Green, Plate 5.

*Peduncle.* — Length—long. Aspect—prickly. Color—Oxblood Red, Plate 1.

*Opening*—Opens up well. Is not affected by adverse weather conditions.

Bloom:

*Size.*—Large. Average size when fully expanded, 5" to 5½".

*Borne.*—Singly and several together.

*Stems.*—Medium length; strong.

*Form.* — When first open, cupped. Permanence—flattens.

*Petalage.* — Very double (many petals and stamens hidden). Number of petals under normal conditions, 50.

*Color.*—Center of flower—Empire Yellow, Plate 4. Outer petals—Barium Yellow, Plate 16. Base of petals (aiglet)—Lemon Chrome, Plate 4. Inside of petals—Pinard Yellow, Plate 4. Reverse of petals—Naphthalene Yellow, Plate 16. General tonality from a distance—Pinard Yellow, Plate 4.

*Discoloration.*—General tonality at end of first day—Pinard Yellow, Plate 4. Second day—between Pinard Yellow, Plate 4, and Naphthalene Yellow, Plate 16. Third day—Naphthalene Yellow, Plate 16.

Petals:

*Texture.*—Thick. Is not affected by wet or hot weather.

*Appearance.*—Inside—satiny; outside—shiny.

*Form.*—Oval.

*Arrangement.*—Informal (with "rags" in center). Petaloids in center—many; large.

*Persistence.*—Drop off cleanly.

*Fragrance.*—Moderate. Nature—fruity (Russet apple).

*Lasting quality.*—On the plant and as cut flower—long.

Genital organs:

*Stamens, anthers.*—Large; many. Color—Picric Yellow, Plate 4, edged with Acajou Red, Plate 13. Arrangement—regular around styles.

*Stamens, filaments (threads).*—Long. Color—Apricot Yellow, Plate 4.

*Pollen.*—Color—Maize Yellow, Plate 4.

*Styles.*—Bunched, uneven length; medium length; thin.
*Stigmas.*—Color—Martius Yellow, Plate 4.
*Ovaries.*—All enclosed in calyx.

*Plant.*

Form: Bush.
Growth: Vigorous; upright.
Foliage: 5 to 7 leaflets.
*Size.*—Large.
*Quantity.*—Abundant.
*Color.*—New foliage: Upper side—Parrot Green, Plate 6; serrations and mid-rib, Oxblood Red, Plate 1. Under side—Oil Green, Plate 5, overcast with Oxblood Red, Plate 1. Old foliage: Upper side—Dark Cress Green, Plate 31. Under side—Light Hellebore Green, Plate 17.
*Shape.*—Oval.
*Texture.*—Upper side—leathery; glossy; under side—smooth. Ribs and veins—ordinary.
*Edge.*—Serrated (saw toothed).
*Serration.*—Single; small.
*Leaf stem.*—Color—Biscay Green, Plate 17. Under side—prickles.

*Stipules.*—Long; bearded.
*Disease resistance.*—Resistant.
Wood:
*New wood.*—Color—Mahogany Red, Plate 2. Bark—smooth.
*Old wood.*—Color—Cress Green, Plate 31. Bark—smooth.
Thorns:
*Thorns.*—Quantity—on main stalks from base and on laterals from stalk, ordinary. Form—broad base; medium length; hooked downward. Color when young—Oxblood Red, Plate 1. Position—irregular.
*Prickles.*—Quantity—on main stalks and on laterals, none.
*Short needles.*—Quantity—on main stalks and on laterals, none.

I claim:

A new and distinct variety of rose plant characterized as to novelty by the yellow color of its blooms; the unusually long peduncle; the color of the stamens and its glossy and leathery foliage, substantially as shown and described.

EDWARD BURTON LE GRICE.

No references cited.